(12) United States Patent
Eymery et al.

(10) Patent No.: US 11,730,881 B2
(45) Date of Patent: Aug. 22, 2023

(54) PACKAGING FOR MEDICAL DEVICES

(71) Applicant: Becton Dickinson France, Le Pont de Claix (FR)

(72) Inventors: Anaïs Eymery, Saint-Georges-de-Commiers (FR); Clémentine Le Loc'h, Meylan (FR)

(73) Assignee: Becton Dickinson France, Le Pont-de-Claix (FR)

( * ) Notice: Subject to any disclaimer, the term of this patent is extended or adjusted under 35 U.S.C. 154(b) by 0 days.

(21) Appl. No.: 17/792,581

(22) PCT Filed: Jan. 14, 2021

(86) PCT No.: PCT/EP2021/050611
§ 371 (c)(1),
(2) Date: Jul. 13, 2022

(87) PCT Pub. No.: WO2021/144324
PCT Pub. Date: Jul. 22, 2021

(65) Prior Publication Data
US 2023/0056837 A1    Feb. 23, 2023

(30) Foreign Application Priority Data
Jan. 15, 2020   (EP) .................................... 20305023

(51) Int. Cl.
*A61M 5/00*     (2006.01)
*B65D 77/20*    (2006.01)

(52) U.S. Cl.
CPC ......... *A61M 5/002* (2013.01); *B65D 77/2032* (2013.01)

(58) Field of Classification Search
CPC ......... A47G 19/03; A61M 5/00; A61M 5/002; B65D 77/20; B65D 77/2032
(Continued)

(56) References Cited

U.S. PATENT DOCUMENTS 4,469,258 A * 9/1984 Wright ............... B65D 77/2032
229/125.05
4,589,568 A * 5/1986 Ito ......................... B29C 66/723
220/359.3

(Continued)

FOREIGN PATENT DOCUMENTS

EP    2085213 A1    8/2009

*Primary Examiner* — Bryon P Gehman
(74) *Attorney, Agent, or Firm* — The Webb Law Firm

(57) ABSTRACT

A packaging for medical devices, including a tub provided with a peripheral wall delimiting an upper opening, a sealing cover sealable on the upper opening of the tub, and a sealing film adapted to be positioned on the upper face of the sealing cover. The sealing film, including a protective foil, an adhesive layer extending over the protective foil, and a peelable sheet having a first portion extending over the adhesive layer opposite to a first portion of the protective foil. The first portions of the protective foil and peelable sheet are arranged in a retracted position uncovering the sealing cover. A second portion of the protective foil, distinct from the first portion, is bonded to the sealing cover and/or to the tub by the adhesive layer, and a second portion of the peelable sheet, separated from said second portion of the protective foil, is arranged so as to be pullable by a user to progressively separate the first portion of the peelable sheet from the first portion of the protective foil to an extended position wherein the protective foil adheres to the sealing cover.

13 Claims, 2 Drawing Sheets

(58) Field of Classification Search
USPC .............................. 206/363–370; 220/359.3
See application file for complete search history.

(56) References Cited

U.S. PATENT DOCUMENTS

| | | | | |
|---|---|---|---|---|
| 5,160,767 | A | * | 11/1992 | Genske ................... B32B 27/08 |
| | | | | 220/359.3 |
| 8,807,373 | B1 | * | 8/2014 | Russell ................... A47G 23/06 |
| | | | | 220/359.1 |
| 2002/0172834 | A1 | | 11/2002 | Rivett et al. |
| 2013/0020328 | A1 | | 1/2013 | Duan et al. |

* cited by examiner

PACKAGING FOR MEDICAL DEVICES

CROSS-REFERENCE TO RELATED APPLICATIONS

This application is the United States national phase of International Application No. PCT/EP2021/050611 filed Jan. 14, 2021, and claims priority to European Patent Application No. 20305023.2 filed Jan. 15, 2020, the disclosures of which are hereby incorporated by reference in their entirety.

BACKGROUND OF THE DISCLOSURE

The disclosure relates to a packaging for medical devices.

DESCRIPTION OF RELATED ART

Medical devices, such as medical containers (typically syringe barrels), stoppers or the like, often have to be transported from one site to another, when they are manufactured in one site and filled in another site, or, less frequently, when they are manufactured and filled in the same site and must be delivered, once filled, to another site.

For this transportation, the medical devices are usually put in a packaging comprising a packaging tub, hereinafter "tub", that contains a grouping tray or nest, hereinafter "nest", that is substantially parallel to the bottom of the tub and that lays on a peripheral flange of the tub. The nest receives and supports the medical devices in a vertical position.

When the packaging is delivered to the pharmaceutical filling plant, the nest is placed into the tub which is sealed with a sealing cover or sheet of porous material and sterilized. The tub is then placed in a sealed plastic bag that ensures that the empty medical devices are not contaminated during transportation and storage.

Standard sealing covers may be paper, or covers made of Tyvek®, which is a porous film made of overlapped layers of high-density polyethylene fibers. This forms a barrier against microbials, viruses, and bacteria, etc. . . . , but allows gas such as ethylene oxide (EtO) and water vapor to go through. As such, sealing covers made of Tyvek® are useful for EtO sterilization in that they maintain sterility inside the tub.

However, they do not prevent other gases from entering the tub such as hydrogen peroxide during the vaporized hydrogen peroxide (acronym VHP) decontamination process. As a result, hydrogen peroxide may thus enter the tub and contaminate the nest and the medical devices contained inside.

A solution is to manually position a protective foil, usually a plastic sheet or a metallic sheet typically comprising aluminum, on the sealing cover in Tyvek®, thereby covering said sealing cover and preventing contamination of the inner volume of the tub by hydrogen peroxide.

However, manual positioning of the protective foil on the sealing cover is time consuming. In addition, the positioning of the protective foil relative to the sealing cover has to be precise in order to ensure optimal sealing, and any misalignment may lead to contamination of the nest and the medical devices. Moreover, the tub preparation step for the decontamination process of the tub is long and requires additional equipment.

SUMMARY OF THE DISCLOSURE

The disclosure aims to provide a packaging for medical devices, especially for medical containers such as syringe barrels for example, that overcomes the drawbacks of the known ones.

The disclosure especially aims to provide such a packaging for medical devices where the protective foil is quickly and easily set up on the tub.

The disclosure also aims to provide such a packaging which reduces the risks of misalignment of the protective foil relative to the sealing cover when setting up said protective foil.

The disclosure also aims to reduce the need of equipment required for the decontamination process of the tub.

To this end, one object of the disclosure is a packaging for medical devices, comprising a tub provided with a peripheral wall delimiting an upper opening, a sealing cover sealable on the upper opening of the tub, and a sealing film adapted to be positioned on the upper face of the sealing cover, the packaging being mainly characterized in that the sealing film comprises:
  a protective foil,
  an adhesive layer extending over the protective foil,
  a peelable sheet having a first portion extending over the adhesive layer opposite to a first portion of the protective foil,
  wherein said first portions of the protective foil and peelable sheet are arranged in a retracted position uncovering the sealing cover,
  wherein a second portion of the protective foil, distinct from the first portion, is bonded to the sealing cover and/or to the tub by the adhesive layer, and a second portion of the peelable sheet, separated from said second portion of the protective foil, is arranged so as to be pullable by a user to progressively separate the first portion of the peelable sheet from the first portion of the protective foil to an extended position wherein the protective foil adheres to the sealing cover.

According to other optional features of the packaging of the disclosure:
  the first portions of the protective foil and peelable sheet are rolled around themselves in the retracted position;
  the second portion of the protective foil that is bonded to the sealing cover and/or to the tub is attached to a first wall of the peripheral wall of the tub, and the first portion of the protective foil contacts a second wall of the peripheral wall of the tub, opposite to the first wall relative to the upper opening, when said first portion is in the extended position, thereby covering the upper opening;
  the second portion of the protective foil that is bonded to the sealing cover and/or to the tub by the adhesive layer is attached to a flange of the tub via the adhesive layer;
  the second portion of the protective foil is attached to a top side of the flange of the tub;
  the top side of the flange is left uncovered by the sealing cover, and the second portion of the protective foil attached to a top side of the flange is attached to said flange via the adhesive layer;
  the top side of the flange is covered by the sealing cover, and the second portion of the protective foil attached to a top side of the flange is attached to the sealing cover via the adhesive layer;
  the second portion of the protective foil is attached to a bottom side of the flange of the tub;

the first portions of the protective foil and peelable sheet arranged in a retracted position form a retracted structure that is located below the flange of the tub, near the bottom side of the flange; in that way, the retracted structure faces the bottom side of the flange;

the second portion of the peelable sheet comprises a tab;

the protective foil comprises one or more layers selected from the group consisting of a metallic layer such as an aluminum layer, a plastic layer such as PE, PET, and a paper layer.

BRIEF DESCRIPTION OF THE DRAWINGS

Further features and advantages of the disclosure will become apparent from the detailed description to follow, with reference to the appended drawings, in which.

DETAILED DESCRIPTION

Figure 1:
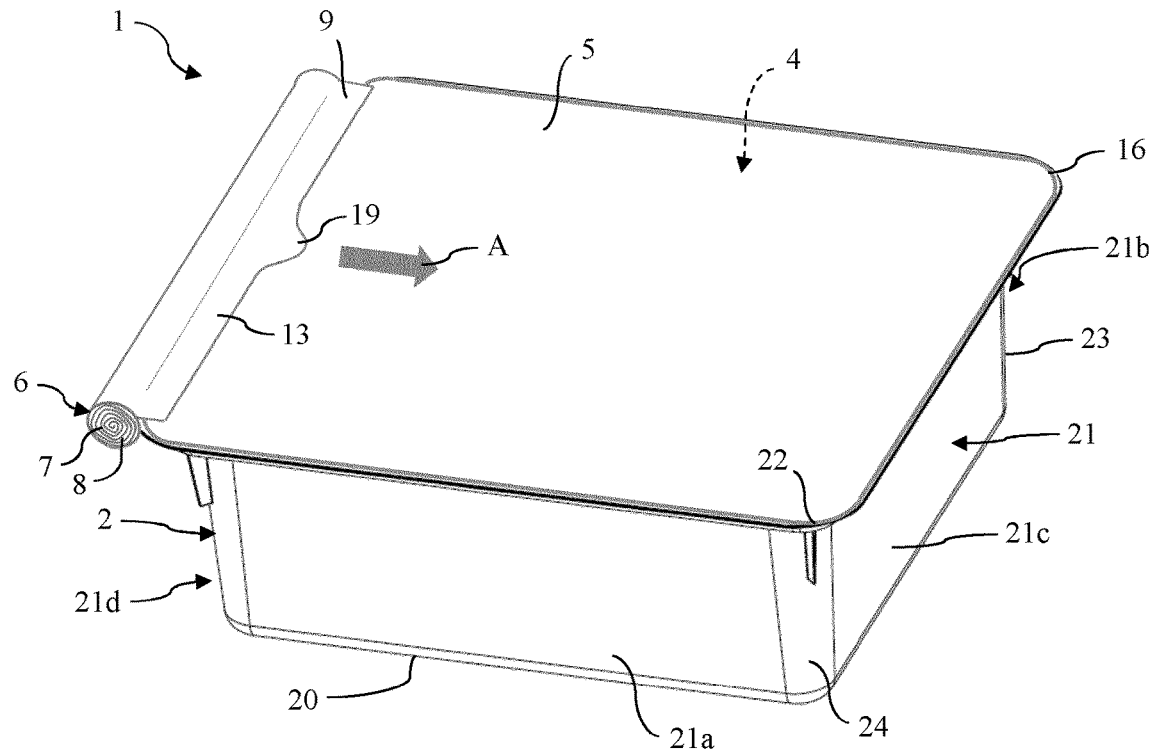
FIG. 1 is a general perspective view of the packaging of the disclosure, comprising a tub, a sealing cover, and a sealing film in a retracted position.

The disclosure relates to a packaging for medical devices. An embodiment of the packaging is represented in FIGS. 1 to 4.

The packaging 1 comprises a tub 2 provided with a peripheral wall 21.

The tub 2 comprises a body adapted to contain a nest that supports the medical devices.

As illustrated in FIGS. 1 to 4, the tub 2 as a general cubic or parallelepiped shape, and comprises a bottom 20, and a peripheral wall 21 comprising two longitudinal walls 21a, 21b substantially parallel to each other and two lateral walls 21c, 21d substantially parallel to each other that extend vertically from the bottom.

In this respect, the terms "lower" and "upper" in the present text relates to an object that is respectively closer and farther from the bottom of the tub.

Besides, the term "horizontal" in the present text relates to an object that lies in a plane parallel to the bottom of the tub, whereas "vertical" relates to an object that is oriented in a direction perpendicular to the bottom of the tub.

Moreover, the terms "longitudinal" and "transversal" designate respectively the length (along the two longitudinal walls) and the width (along the two transversal walls) of the tub.

The peripheral wall 21 of the tub comprises a lower peripheral wall 14 in connection with the bottom of the tub, and an upper peripheral wall 15 extending from the lower peripheral wall 14 and separated from the latter by a shoulder 19. The upper peripheral wall 15 delimits an upper opening 4 and includes a peripheral outer flange 16 levelled with the upper opening 4.

The tub 2 is preferably integrally formed by a single part of molded plastic material such as polystyrene or polypropylene for example.

The packaging 1 further comprises a sealing cover 5 sealable on the upper opening 4 of the tub, in particular on the outer flange 16, in order to close the tub, and a sealing film 6 adapted to be positioned on an upper face of the sealing cover.

The sealing cover 5 is preferably formed by a sheet of porous material, for example a Tyvek® sheet and may be coated with a heat sealable material.

The sealing film 6 comprises a multilayer structure which comprises a protective foil 7, an adhesive layer 8 extending over the protective foil, and a peelable sheet 9 which extends over the adhesive layer 8. The multilayer structure of the sealing film is particularly visible in FIG. 4.

The protective foil 7 prevents certain gases from entering the tub during corresponding steps of the conditioning of the packaging, such as hydrogen peroxide during the vaporized hydrogen peroxide (acronym VHP) decontamination process for example.

The protective foil 7 preferably comprises one or more layers selected from the group consisting of a metallic layer such as an aluminum layer, a plastic layer such as polyethylene (PE), polyethylene terephthalate (PET), and a paper layer.

Figure 4:
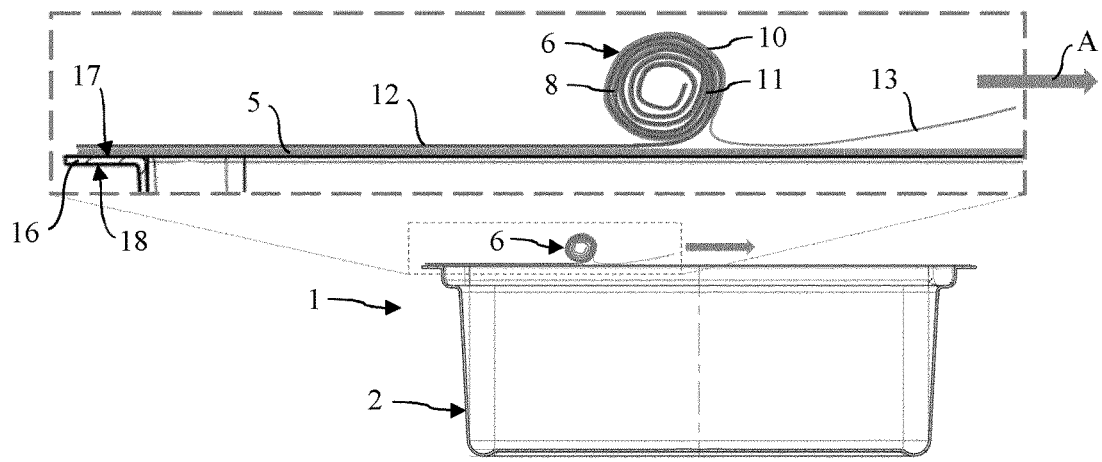
FIG. 4 is an enlarged view of a portion of FIG. 3.

The peelable sheet 9 comprises a first portion 10 that extends over the adhesive layer 8 opposite to a first portion 11 of the protective foil 7. This is illustrated in FIG. 4.

The peelable sheet 9 is adapted to be peeled off from the protective foil 7, so as to expose the adhesive layer 8 that covers the first portion of the protective foil.

The peelable sheet preferably comprises paper and/or plastic.

The first portion 11 of the protective foil 7 and the first portion 10 of the peelable sheet 9 are arranged in a retracted position uncovering the sealing cover 5. Since the adhesive layer 8 is located between the first portions 10, 11 of the protective foil 7 and the peelable sheet 9, said adhesive layer is also arranged in the retracted position.

The first portion 11 of the protective foil 7 and the first portion 10 of the peelable sheet 9 are fixed or bonded together via the adhesive layer 8.

The retracted structure thus formed comprises a stack of the first portion 11 of the protective foil 7, and the first portion 10 of the peelable sheet 9 separated by the adhesive layer 8.

According to a preferred embodiment, the first portions 10, 11 of the protective foil 7 and peelable sheet 9 are rolled around themselves in the retracted position. The first portions 10, 11 of the protective foil 7 and peelable sheet 9 thereby form a cylinder or a scroll that may present a cross-section forming a spiral. Since the adhesive layer 8 is located between the first portions 10, 11 of the protective foil 7 and the peelable sheet 9, said adhesive layer is also rolled in the retracted position.

According to another embodiment, the first portions 10, 11 of the protective foil 7 and peelable sheet 9 are folded on themselves in the retracted position. In that way, the retracted structure thus formed comprises several folds, each fold comprising the first portion 11 of the protective foil 7 and the first portion 10 of the peelable sheet 9 separated by the adhesive layer 8.

Other arrangements of the protective foil 7 and peelable sheet 9 in the retracted position are possible without departing from the scope of the disclosure. For example, the protective foil 7 and the peelable sheet 9 may be folded a number of times to form an accordion.

A second portion 12 of the protective foil 7 is free, that is, not covered by the peelable sheet 9.

The retracted structure may be positioned above the peripheral outer flange 16 of the tub 2, meaning at the top side 17 of the flange 16, or below the flange, meaning at the bottom side 18 of the flange (this is the positioning represented in FIG. 2), or next to the flange opposite to the opening relative to the flange (this is the positioning represented in FIG. 1). One advantage of positioning the retracted structure near the bottom side 18 of the flange is that said retracted structure does not interfere with the stacking of the tubs 2.

According to a first embodiment, the second portion 12 of the protective foil is fixed or bonded to the peripheral outer flange 16 of the tub 2, meaning at the top side 17 of said peripheral outer flange 16. The outer flange 16 may be that of one of the two longitudinal walls 21a, 21b or transversal walls 21c, 21d of the tub 2, or a corner 22 between a longitudinal wall and a transversal wall of the tub.

In this first embodiment, the second portion 12 of the protective foil 7 may be attached directly to the flange 16 of the tub via the adhesive layer 8. There is no sealing cover in between, as said sealing cover 5 does not cover the flange 16, but is adjacent to the second portion 12 of the protective foil 7 and covers the upper opening 4 of the tub.

Alternatively, in this first embodiment, the second portion 12 of the protective foil 7 may be attached to the sealing cover 5 via the adhesive layer 8. The sealing cover 5 covers the flange 16 and is located between the protective foil 7 and the flange 16.

According to a second embodiment, the second portion 12 of the protective foil is fixed to the bottom side 18 of the peripheral outer flange 16 of the tub 2.

In this second embodiment, the second portion 12 of the protective foil 7 is attached directly to the flange 16 of the tub via the adhesive layer 8.

Regardless of the embodiment of the disclosure, the second portion 12 of the protective foil is preferably attached directly to the tub by the adhesive layer, without the sealing cover 5 in between. The bonding is indeed better compared to the bonding of the protective foil with the sealing cover 5.

Figure 2:
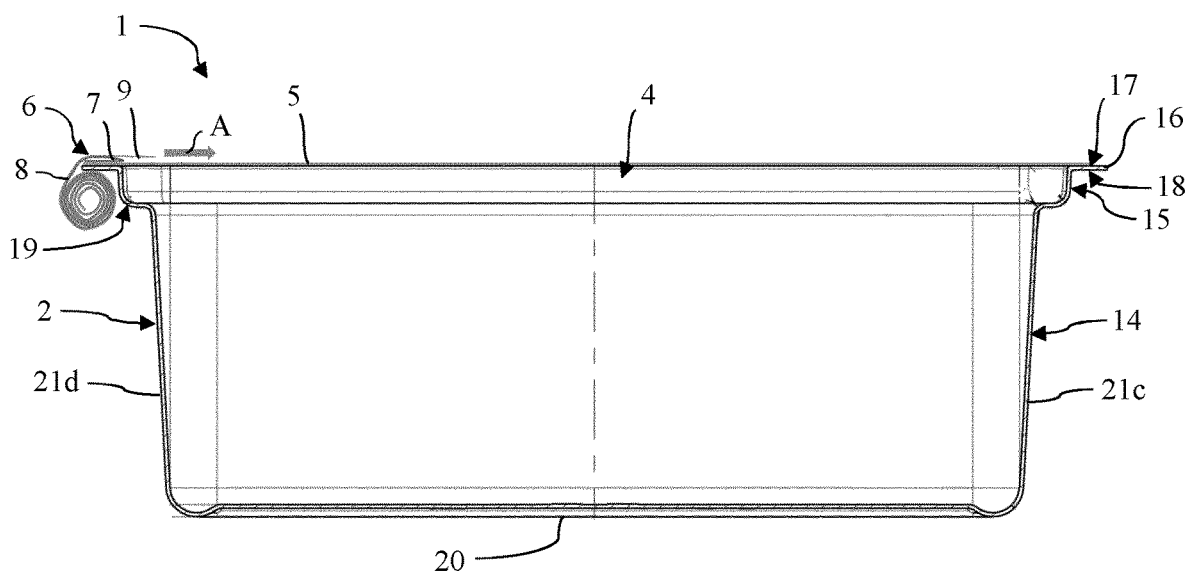
FIG. 2 is a side view of the packaging of FIG. 1.
Figure 3:
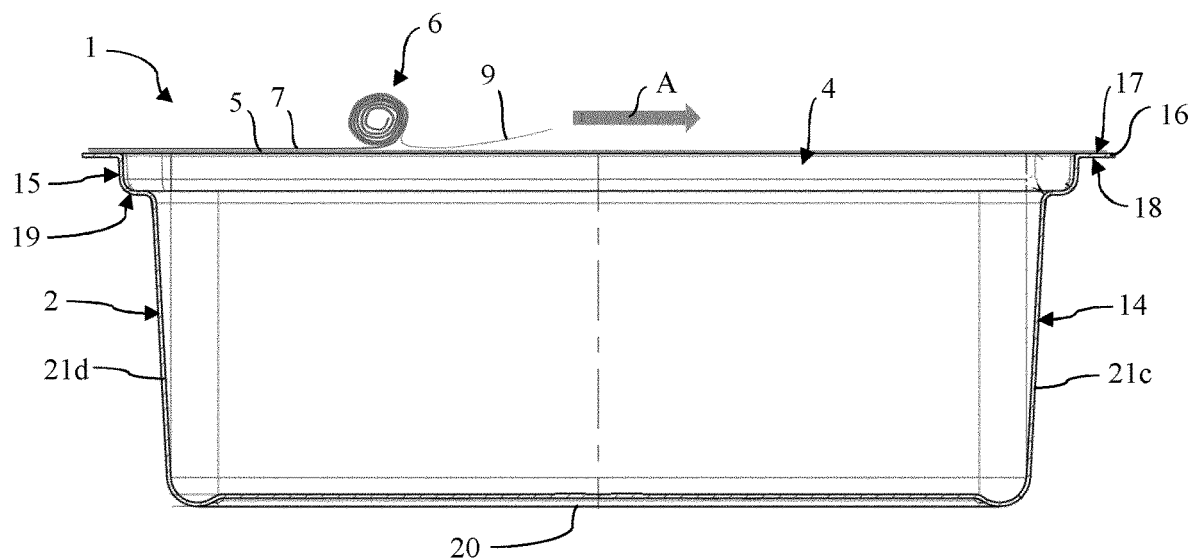
FIG. 3 is a side view of the packaging, wherein the protective foil transitions from the retracted position to the extended position where the protective foil adheres to the sealing cover.

As illustrated in FIGS. 1 and 2, the peelable sheet 9 comprises a second portion 13 that is separated from the second portion 12 of the protective foil. "Separated" means that the second portion 13 is not in contact with the second portion 12 of the protective foil.

The second portion 13 of the peelable sheet protrudes from the retracted structure formed by the first portions 10, 11 of the protective foil 7 and the peelable sheet 9 in the retracted position. In other terms, in the retracted position, the second portion 13 extends toward the wall of the tub that is opposite to the wall to which the sealing film 6 is attached.

The second portion 13 of the peelable sheet 9 is arranged so as to be pullable by a user, to progressively separate the first portion 10 of the peelable sheet 9 from the first portion 11 of the protective foil to an extended position wherein the protective foil 7 adheres to the sealing cover 5. The direction of pulling the second portion 13 for unfolding the peelable sheet 9 and the protective foil 7 along with the adhesive layer 8, thereby making them transition from the retracted position to the extended position is represented by the arrow A in FIGS. 1 to 4.

More precisely, in the extended position, both the first portion 11 and the second portion 12 of the protective foil 7 adhere to the sealing cover 5 via the adhesive layer 8. Accordingly, in the extended position, the peelable sheet 9 has been removed from the sealing film and may be disposed of.

According to a preferred embodiment, the second portion 13 of the peelable sheet 9 comprises a tab, as illustrated in FIG. 1. Such tab can be easily and quickly grabbed by the user for extending the protective foil over the sealing cover.

The positioning of the protective foil 7 over the sealing cover 5 will be described in the following.

Initially, the first portion 11 of the protective foil 7 and the first portion 10 of the peelable sheet 9 are arranged in the retracted position, thereby leaving the sealing cover 5 previously sealed on the upper opening 4 of the tub uncovered.

The user grabs the second portion 13 of the peelable sheet 9 and pulls it in a horizontal direction, that is, in a direction opposite to the first portions 10, 11 of the protective foil and the peelable sheet.

The first portion 10 of the peelable sheet progressively separates from the first portion 11 of the protective foil, and extends to an extended position, thereby progressively covering and adhering to the sealing covering 5 via the adhesive layer 8.

According to the embodiment where the second portion 12 of the protective foil 7 is fixed to the sealing cover 5 at a first longitudinal wall 21d (respectively transversal wall 21a) of the peripheral wall of the tub, the protective foil 7 extends toward the second longitudinal wall 21c (respectively transversal wall 21b), opposite to the first wall relative to the upper opening 4 of the tub, and along the two transversal walls 21a, 21b (respectively longitudinal walls 21c, 21d), until reaching said second longitudinal wall 21c.

According to the embodiment where the second portion 12 of the protective foil 7 is fixed to the sealing cover 5 at a first corner 22 of the peripheral wall of the tub, the protective foil 7 extends toward a second corner 23, opposite to the first corner relative to the upper opening 4 of the tub, and along the four walls 21a, 21b, 21c, 21d of the tub passing by the two remaining corners 24 until reaching said second corner 23.

The protective foil 7 thus completely covers the sealing cover 5 and adheres thereto thanks to the adhesive layer 8. The peelable sheet 9 that has been removed may be disposed of.

After removal of the peelable sheet 9, the top surface of the sealing cover 5 that seals the upper opening 4 of the packaging is covered by the protective sheet 7 bonded thereto by the adhesive layer 8 in between.

The positioning of the protective foil over the sealing cover that has been described can be carried out quickly and easily, and reduces the risk of misalignment of the protective foil relative to the upper opening of the tub that may occur with the known packagings, due to a portion of the protective foil being already bonded to a corresponding portion of the sealing cover before use in the packaging of the disclosure.

Moreover, from a practical point of view, since the protective foil is already bonded to the sealing cover, there is no need to purchase said protective foil separately, which simplifies the tub preparation for the decontamination process.

The invention claimed is:
1. A packaging for medical devices, comprising a tub provided with a peripheral wall delimiting an upper opening, a sealing cover sealable on the upper opening of the tub, and a sealing film adapted to be positioned on the upper face of the sealing cover,
the sealing film comprising:
a protective foil,
an adhesive layer extending over the protective foil,
a peelable sheet having a first portion extending over the adhesive layer opposite to a first portion of the protective foil,
wherein said first portion of the protective foil and said first portion of the peelable sheet are arranged in a retracted position uncovering the sealing cover, wherein a second portion of the protective foil, distinct from the first portion of the protective foil, is bonded to at least one of the sealing cover and the tub by the adhesive layer, and a second portion of the peelable sheet, separated from said second portion of the protective foil, is arranged so as to be pullable by a user to progressively separate the first portion of the peelable sheet from the first portion of the protective foil to an extended position wherein the protective foil adheres to the sealing cover.

2. The packaging of claim 1, wherein the first portion of the protective foil and the first portion of the peelable sheet are rolled around themselves in the retracted position.

3. The packaging of claim 1, wherein the second portion of the protective foil that is bonded to at least one of the sealing cover and the tub is attached to a first wall of the peripheral wall of the tub, and the first portion of the protective foil contacts a second wall of the peripheral wall of the tub, opposite to the first wall relative to the upper opening, when said first portion of the protective foil in the extended position, thereby covering the upper opening.

4. The packaging of claim 1, wherein the second portion of the protective foil that is bonded to at least one of the sealing cover and the tub by the adhesive layer is attached to a flange of the tub via the adhesive layer.

5. The packaging of claim 4, wherein the second portion of the protective foil is attached to a top side of the flange of the tub.

6. The packaging of claim 5, wherein the top side of the flange is left uncovered by the sealing cover, and the second portion of the protective foil attached to the top side of the flange is attached to said flange via the adhesive layer.

7. The packaging of claim 5, wherein the top side of the flange is covered by the sealing cover, and the second portion of the protective foil attached to the top side of the flange is attached to the sealing cover via the adhesive layer.

8. The packaging of claim 4, wherein the second portion of the protective foil is attached to a bottom side of the flange of the tub.

9. The packaging of claim 1, wherein the first portion of the protective foil and the first portion of the peelable sheet arranged in the retracted position form a retracted structure that is located below the flange of the tub, near the bottom side of the flange.

10. The packaging claim 1, wherein the second portion of the peelable sheet comprises a tab.

11. The packaging of claim 1, wherein the protective foil comprises one or more layers selected from the group consisting of a metallic layer, a plastic layer and a paper layer.

12. The packaging of claim 11, wherein the protective foil comprises at least one aluminum layer.

13. The packaging of claim 11, wherein the protective foil comprises at least one layer made of PE or PET.

* * * * *

UNITED STATES PATENT AND TRADEMARK OFFICE
CERTIFICATE OF CORRECTION

PATENT NO. : 11,730,881 B2
APPLICATION NO. : 17/792581
DATED : August 22, 2023
INVENTOR(S) : Anaïs Eymery et al.

It is certified that error appears in the above-identified patent and that said Letters Patent is hereby corrected as shown below:

In the Claims

Column 7, Line 21, Claim 3, delete "foil" and insert -- foil is --

Column 8, Line 18, Claim 10, delete "packaging" and insert -- packaging of --

Signed and Sealed this
Tenth Day of October, 2023

Katherine Kelly Vidal
*Director of the United States Patent and Trademark Office*